United States Patent [19]

Bright

[11] Patent Number: 4,474,768

[45] Date of Patent: Oct. 2, 1984

[54] N-METHYL 11-AZA-10-DEOXO-10-DIHYDROERYTHROMYCIN A, INTERMEDIATES THEREFOR

[75] Inventor: Gene M. Bright, Groton, Conn.

[73] Assignee: Pfizer Inc., New York, N.Y.

[21] Appl. No.: 441,981

[22] Filed: Nov. 15, 1982

Related U.S. Application Data

[63] Continuation-in-part of Ser. No. 399,401, Jul. 19, 1982, abandoned.

[51] Int. Cl.$^3$ ................... A61K 31/71; C07H 17/08
[52] U.S. Cl. ................................ 424/180; 536/7.4
[58] Field of Search ..................... 536/7.4; 424/180

[56] References Cited

U.S. PATENT DOCUMENTS 3,928,387 12/1975 Kierstead et al. ............... 536/7.4
4,110,531 8/1978 Sciavolino ...................... 536/7.4
4,283,527 8/1981 Sciavolino ...................... 536/7.4
4,328,334 5/1982 Kobrehel et al. ................ 536/7.4

FOREIGN PATENT DOCUMENTS 892357 7/1982 Belgium .

OTHER PUBLICATIONS

Migridichian *Organic Synthesis*, vol. 1, New York: Reinhold Pub. Corp. 1957, p. 476.

Greene, "Protective Groups in Organic Synthesis", John Wiley & Sons, Inc., N.Y., 1981, p. 281.

*Primary Examiner*—Johnnie R. Brown
*Assistant Examiner*—Elli Peselev
*Attorney, Agent, or Firm*—Charles J. Knuth; Albert E. Frost; Peter C. Richardson

[57] ABSTRACT

Antibacterial N-methyl 11-aza-10-deoxo-10-dihydroerythromycin A and pharmaceutically acceptable acid addition salts thereof, intermediates therefor, and processes for their preparation.

8 Claims, No Drawings

N-METHYL 11-AZA-10-DEOXO-10-DIHYDROERYTHROMYCIN A, INTERMEDIATES THEREFOR

CROSS-REFERENCE TO RELATED APPLICATION

This application is a continuation-in-part of copending application Ser. No. 399,401, filed July 19, 1982, now abandoned.

BACKGROUND OF THE INVENTION

This invention relates to a novel derivative of 11-aza-10-deoxo-10-dihydroerythromycin A useful as an antibacterial agent, to intermediates therefor, and to processes for their preparation. More particularly it relates to the N-methyl derivative of 11-aza-10-deoxo-10-dihydroerythromycin A, to pharmaceutically acceptable acid addition salts thereof, and to certain alkanoyl derivatives thereof useful as antibacterial agents, to intermediates therefor, and to processes for their preparation.

Erythromycin A is a macrolide antibiotic produced by fermentation and described in U.S. Pat. No. 2,653,899. Numerous derivatives of erythromycin A have been prepared in efforts to modify its biological and/or pharmacodynamic properties. Erythromycin A esters with mono- and dicarboxylic acids are reported in Antibiotics Annual, 1953–1954, Proc. Symposium Antibiotics (Washington, D.C.), pages 500–513 and 514–521, respectively. U.S. Pat. No. 3,417,077 describes the cyclic carbonate ester of erythromycin A, the reaction product of erythromycin A and ethylene carbonate, as an active and antibacterial agent.

U.S. Pat. No. 4,328,334, issued May 4, 1982, describes 11-aza-10-deoxo-10-dihydroerythromycin A, certain N-acyl- and N-(4-substituted benzenesulfonyl) derivatives thereof having antibacterial properties, and a process for their preparation.

The alkylation of primary and/or secondary amine groups of compounds which include a tertiary amine group is generally complicated. However, it is common practice to protect tertiary amine groups in such compounds by converting them to N-oxides prior to alkylation (Greene, "Protective Groups in Organic Synthesis", John Wiley & Sons, Inc., N.Y., 1981, pg. 281).

SUMMARY OF THE INVENTION

It has now been found that the N-methyl derivative of 11-aza-10-deoxo-10-dihydroerythromycin A and its 2'-, 4"- and/or 2',4"-acetyl-, propionyl- and 3-carbethoxypropionyl derivatives are effective antibacterial agents against gram-positive and gram-negative bacteria. The compounds have formula I

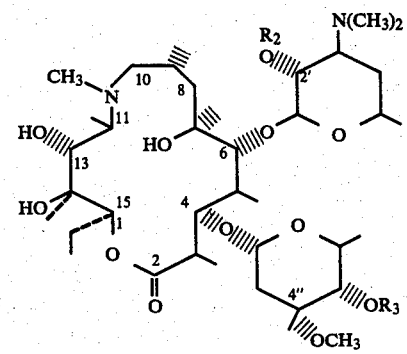

wherein $R_2$ is hydrogen, alkanoyl having from 2 to 3 carbon atoms or 3-carbethoxypropionyl; and $R_3$ is hydrogen, alkanoyl having from 2 to 3 carbon atoms or 3-carbethoxypropionyl.

Also valuable for the same purpose as formula I compounds are the pharmaceutically acceptable acid addition salts thereof. Included among said salts, but by no means limited to said salts, are those enumerated below: hydrochloride, hydrobromide, sulfate, phosphate, formate, acetate, propionate, butyrate, citrate, glycolate, lactate, tartrate, malate, maleate, fumarate, gluconate, stearate, mandelate, pamoate, benzoate, succinate, lactate, p-toluenesulfonate and aspartate.

This invention also includes the intermediates of formulae II, III and III-A:

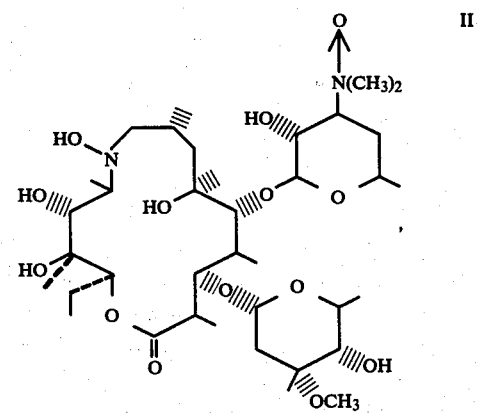

and

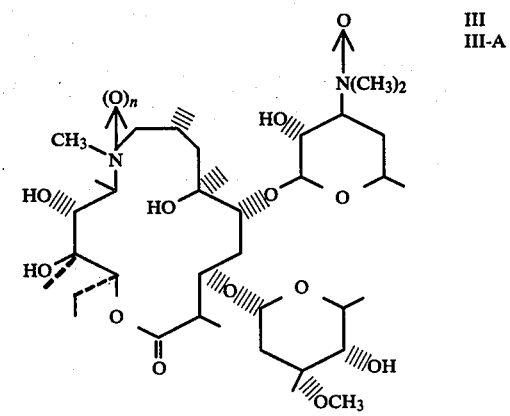

$n = 1$

-continued n = 0

The compounds of this invention of formula I can be named as N-methyl-11-aza-4-O-(L-cladinosyl)-6-O-(D-desosaminyl)-15-ethyl-7,13,14-trrihydroxy-3,5,7,9,12,14-hexamethyloxacyclopentadecane-2-ones. However, for simplicity, they are referred to herein as N-methyl derivatives of 11-aza-10-deoxo-10-dihydro-erythromycin A, the nomenclature used in U.S. Pat. No. 4,328,334.

The compound of formula II ($R_2=R_3=H$) is named in like manner as N-hydroxy-11-aza-10-deoxo-10-dihydroerythromycin A N'-oxide, the term "N'-oxide" referring to oxide formation on the dimethylamino group of the desosaminyl moiety. The alkylated structure of formula III ($R_2=R_3=H$) is named as N-methyl-11-aza-10-deoxo-10-dihydroerythromycin bis N-oxide. The stereochemistry at the 11-aza atom of formula III is not yet known. However, said formula III is intended to embrace the diastereomers.

As an alternative to the nomenclature used above, the parent compound of formula IV below can be named as 9-deoxo-9a-aza-9a-homoerythromycin A. Using this system the compounds of formula I wherein each of $R^2$ and $R^3$ is hydrogen is named 9-deoxo-9a-methyl-9a-aza-9a-homoerythromycin A.

Compounds of formula I and pharmaceutically acceptable acid addition salts thereof are effective antibacterial agents against gram-positive microorganisms, e.g. *Staphylococcus aureus* and *Streptococcus pyogenes*, and against gram-negative microorganisms, e.g. *Pasturella multocida* and *Neisseria sicca*. Additionally, they exhibit significant activity against *Haemophilus in vitro*. The N-methyl derivative (formula I, $R_2=R_3=H$), is superior to erythromycin A and 11-aza-10-deoxo-10-dihydroerythromycin A in its in vitro activity against Haemophilus.

The N-methyl derivatives (formula I) surprisingly and unexpectedly exhibit oral activity against gram-positive and gram-negative microorganisms. The N-methyl derivative of formula I ($R_2=R_3=H$) exhibits significant oral activity in vivo whereas no practical oral in vivo activity is exhibited by 11-aza-10-deoxo-10-dihydroerythromycin A.

DETAILED DESCRIPTION OF THE INVENTION

The N-methyl derivative of 11-aza-10-deoxo-10-dihydroerythromycin A (formula I) is prepared from 11-aza-10-deoxo-10-dihydroerythromycin A (formula IV) by the following reaction sequence:

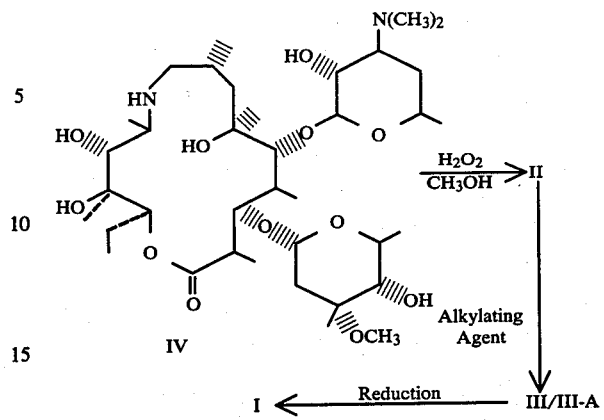

The oxidation of 11-aza-10-deoxo-10-dihydroerythromycin A is conducted in a reaction-inert solvent, i.e., one which does not react with reactants or products to produce undesired substances, under the conditions of the reaction, using as oxidizing agent hydrogen peroxide or a per acid such as peracetic acid, perbenzoic acid, m-chloroperbenzoic acid, permaleic acid and perphthalic acid.

The choice of solvent depends, in part, upon the oxidizing agent used. When using a water soluble oxidizing agent such as hydrogen peroxide or peracetic acid, a water miscible solvent should be used. When using oxidizing agents of low water solubility, e.g. perbenzoic or m-chloroperbenzoic acid, an aqueous reaction mixture is generally avoided in order to maintain a single phase reaction mixture.

Suitable solvents for use with the latter oxidizing agents are methylene chloride, chloroform, ethers, e.g. dioxane, tetrahydrofuran.

The oxidation is carried out at ambient temperature; i.e., from about 18°–25° C., for reaction periods of up to 24 hours. An excess of oxidizing agent is used to ensure maximum conversion of 11-aza-10-deoxo-10-dihydroerythromycin A, the limiting reactant. In general, from about 1.0 mole to about 35 moles of oxidant per mole of said limiting reactant is used. In practice, for the sake of economy, from about 5 to about 15 moles of oxidant are used per mole of the limiting reactant. Hydrogen peroxide is favored as oxidizing agent because of its availability. The amine oxide of formula II is isolated by extraction following removal of destruction of the excess oxidizing agent.

The amine oxide of formula II thus produced is then alkylated by reaction with an appropriate alkylating agent such as methyl iodide or bromide in a reaction-inert solvent and in the presence of an acid acceptor. Representative of reaction-inert solvents useful in this step are methylene chloride, chloroform, tetrahydrofuran and toluene. Suitable acid acceptors are inorganic bases such as alkali metal hydroxides and carbonates, and organic amines such as hindered amine bases, e.g. 2,6-lutidine, said substances being used in at least stoichiometric amount based on the alkylating agent used.

The alkylating agents are generally used in amounts based upon the amine oxide reactant ranging from equimolar to up to 100% excess.

The alkylation reaction, when methyl iodide is used as alkylating agent, is conveniently carried out at ambient temperature. Alkylation by means of methyl bromide is sluggish at ambient temperatures, requiring prolonged reaction periods of several days. When methyl bromide is used elevated temperatures, e.g. up to about 120° C., are favored in order to expedite reaction.

An alternative alkylation procedure comprises the use of dimethyl sulfate in a reaction-inert solvent in the presence of an inorganic base such as those enumerated above. The reaction conditions when using dimethyl sulfate parallel those mentioned above for the methyl halides.

The intermediate products formed by alkylation of the formula II compound are isolated, if desired, by standard procedures such as evaporation of the reaction mixture following water wash thereof to remove inorganic salts. The reduction products (formula I) of said intermediates are also isolated by standard procedures such as extraction.

It has been found that alkylation of the crude product resulting from the oxidation of IV, gives rise to two products; the compound of formula III identified herein as N-methyl-11-aza-10-deoxo-10-dihydroerythromycin A bis-N-oxide III; and the mono oxide (III-A) wherein oxide formation is at the desosaminyl nitrogen. Said compound is referred to herein as N-methyl-11-aza-10-deoxo-10-dihydroerythromycin A desosaminyl-N-oxide.

The above-described intermediates need not be purified prior to their use in subsequent steps of the above reaction sequence. They can be used in crude form, i.e., as is, following their separation from their respective reaction mixtures. From the standpoint of convenience and economy the intermediates are generally not purified prior to their use in the process of this invention.

The third and final step of the reaction sequence, the reduction step, is carried out either catalytically or chemically on the crude product of the alkylation reaction, or on the individual pure alkylated mono- and bis-oxides (IIIA and III). Catalytic reduction is carried out at ambient temperature (e.g. 18°–25° C.) at hydrogen pressures of from about 1 to about 70 atmospheres in a reaction-inert solvent. Higher temperatures and pressures can be used, if desired, but offer no advantages.

Suitable catalysts are the noble metal catalysts, preferably supported, and certain salts thereof such as the oxides. Representative catalysts are Pd/C, Rh/C, PtO$_2$ and Raney nickel. The ratio of catalyst to substrate is not critical, but is generally in the range of from 1:1 to 1:2.

Typical solvents for the reduction step are C$_{1-4}$ alcohols, especially ethanol, ethyl acetate and ethers, e.g. tetrahydrofuran, dioxan.

In addition to the above-mentioned heterogeneous catalytic reduction, homogeneous catalysis using, for example, tris(triphenylphosphine)chlororhodium (I), known as the Wilkinson catalyst, can be used. Suitable solvents for said reaction are those enumerated above in connection with the heterogeneous catalyst procedure and in which the homogeneous catalyst is soluble. The concentration of homogeneous catalyst is not critical but, for reasons of economy, is generally kept at levels of from about 0.01 mole percent to about 10 mole percent by weight based on the substrate.

The hydrogen pressure is not critical but, for the sake of convenience, is generally within the range of from about 1 to about 70 atmospheres.

In the above discussions of heterogeneous and homogeneous catalysis, even though the amounts of catalyst which would be used are not generally considered "catalytic" in the normal usage of this term, they are considered as catalytic here since little or no reaction would occur in their absence.

The temperature of the catalytic reductions, heterogeneous or homogeneous, is not critical, but can vary from about 20° C. to about 100° C. The favored temperature range is from 20° to 80° C.

Chemical reduction of the alkylated amine oxides (III-A and III) is accomplished by means of metal hydrides such as sodium borohydride, sodium cyanoborohydride, pyridine-SO$_3$/potassium iodide, or zinc/glacial acetic acid.

Compounds of formula I wherein R$_2$ and/or R$_3$ are alkanoyl as herein defined are conveniently prepared by standard acylation procedures such as those described by Jones et al., J. Med. Chem. 15, 631 (1972), and by Banaszek et al., Rocy. Chem. 43, 763 (1969). The 2'- and 4''-hydroxy groups are acylated by means of the appropriate acid anhydride [e.g. (R$_2$CO)$_2$O] in pyridine. Solvolysis of the 2',4''-ester with methanol produces the 4''-ester.

Formation of mixed esters, e.g. 2'-acetyl-4''-propionyl-, is readily achieved by acylating the 4''-ester (R$_3$=propionyl) with acetic anhydride in a reaction-inert solvent in the presence of potassium carbonate according to the procedure for mixed esters described by Jones et al. (loc. cit.).

Acid addition salts of the compounds of this invention are readily prepared by treating compounds having formula I with at least an equimolar amount of the appropriate acid in a reaction-inert solvent or, in the case of the hydrochloride salts, with pyridinium hydrochloride. Since more than one basic group is present in a compound of formula I, the addition of sufficient acid to satisfy each basic group permits formation of poly-acid addition salts. When preparing acid addition salts of formula I compounds wherein R$_2$ is alkanoyl, isopropanol is used as solvent to avoid solvolysis of the alkanoyl group. The acid addition salts are recovered by filtration if they are insoluble in the reaction-inert solvent, by precipitation by addition of a non-solvent for the acid addition salt, or by evaporation of the solvent.

A variety of gram-positive microorganisms and certain gram-negative microorganisms, such as those of spherical or ellipsoidal shape (cocci), are susceptible to compounds of formula I. Their in vitro activity is readily demonstrated by in vitro tests against various microorganisms in a brain-heart infusion medium by the usual two-fold serial dilution technique. Their in vitro activity renders them useful for topical application in the form of ointments, creams and the like, for sterilization purposes, e.g. sick-room utensils; and as industrial antimicrobials, for example, in water treatment, slime control, paint and wood preservation.

For in vitro use, e.g. for topical application, it will often be convenient to compound the selected product with a pharmaceutically-acceptable carrier such as vegetable or mineral oil or an emollient cream Similarly, they may be dissolved or dispersed in liquid carriers or solvents, such as water, alcohol, glycols or mixtures thereof or other pharmaceutically-acceptable inert media; that is, media which have no harmful effect on the active ingredient. For such purposes, it will generally be acceptable to employ concentrations of active ingredient of from about 0.01 percent up to about 10 percent by weight based on total composition.

Additionally, many compounds of this invention are active versus gram-positive and certain gram-negative microorganisms in vivo via the oral and/or parenteral routes of administration in animals, including man. Their in vivo activity is more limited as regards susceptible organisms and is determined by the usual procedure which comprises infecting mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the $LD_{100}$ (the lowest concentration of organisms required to produce 100% deaths). Contol tests are simultaneously run in which mice receive inoculum of lower dilutions as a check on possible variation in virulence of the test organism. The test compound is administered 0.5 hour post-inoculation, and is repeated 4, 24 and 48 hours later. Surviving mice are held for 4 days after the last treatment and the number of survivors is noted.

When used in vivo, these novel compounds can be administered orally or parenterally, e.g. by subcutaneous or intramuscular injection, at a dosage of from about 1 mg/kg to about 200 mg/kg of body weight per day. The favored dosage range is from about 5 mg/kg to about 100 mg/kg of body weight per day and the preferred range from about 5 mg/kg to about 50 mg/kg to body weight per day. Vehicles suitable for parenteral injection may be either aqueous such as water, isotonic saline, isotonic dextrose, Ringer's solution or non-aqueous such as fatty oils of vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents; for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

In the Examples presented herein, no effort was made to recover the maximum amount of product produced or to optimize the yield of a given product. The Examples are merely illustrative of the process and of the products obtainable thereby.

EXAMPLE 1

N-Hydroxy-11-aza-10-deoxo-10-dihydroerythromycin A N'-oxide (Formula II)

To a solution of 11-aza-10-deoxo-10-dihydroerythromycin A (10.0 g) in 40 ml of methanol, a total of 50 ml of 30% aqueous hydrogen peroxide was added dropwise while stirring over a 5-10 minute period. After stirring overnight at ambient temperature, the reaction mixture was poured onto a stirred slurry of ice (200 g), ethyl acetate (200 ml), and water (100 ml). Excess hydrogen peroxide was quenched by cautious dropwise addition of saturated aqueous sodium sulfite until a negative starch-iodine test was indicated. The layers were separated; and the aqueous layer was washed twice with 200 ml portions of ethyl acetate. The three organic extracts were combined, dried over anhydrous sodium sulfate, and evaporated to afford crude N-hydroxy-11-aza-10-deoxo-10-dihydroerythromycin A N'-oxide as a colorless foam (8.6 g).

While the crude product proved satisfactory for use in the preparative procedure described below, purification was readily achieved by silica gel chromatography, eluting with a methylene chloride: methanol:concentrated ammonium hydroxide system (12:1:0.1). Progress of the column was followed by thin layer chromatography on silica gel plates using the system methylene chloride:methanol:concentrated ammonium hydroxide (9:1:0.1). The plates were developed with a vanillin spray [ethanol (50 ml): 85% $H_3PO_4$ (50 ml):vanillin (1.0 g)] indicator with heat. $^1$Hnmr (CDCl$_3$) delta 3.21

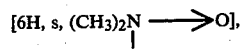

3.39 (3H, s, cladinose $CH_3O$-). MS: major peaks at m/e 576 (ion from desosamine fragmentation), 418 (aglycone ion-minus both sugars). Both peaks are diagnostic for

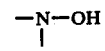

moiety within aglycone.

In like manner, but substituting hydrogen peroxide by an equivalent amount of peracetic acid, the same compound is produced.

EXAMPLE 2

N-Methyl-11-aza-10-deoxo-10-dihydroerythromycin A bis-N-oxide (Formula III)

To a stirred mixture of N-hydroxy-11-aza-10-deoxo-10-dihydroerythromycin A N'-oxide (4.83 g), methylene chloride (100 ml) and solid anhydrous potassium carbonate (69.7 g), was added 15.7 ml (35.8 g) of iodomethane dropwise under nitrogen over two minutes. The mixture was stirred under nitrogen at ambient temperature for 3.5 hours and the solid which formed recovered by filtration. The filter cake was washed with methylene chloride (250 ml), the filtrate and wash solutions were combined, water (300 ml) was added, and the pH of the vigorously stirred mixture adjusted to 11. The organic phase was separated, dried with anhydrous sodium sulfate, and concentrated to afford crude product as a colorless foam (4.36 g).

While the crude product proved satisfactory for use in the reduction procedure described below, purification was readily achieved by the technique commonly known as "Flash" silica gel chromatography [W. Clark Still, et al., *J. Org. Chem.* 43, 2923 (1978)] utilizing 230-400 mesh silica gel (silica gel/crude material about 45/1 by weight), eluting by the "flash technique" with acetone/methanol=4/1 by volume. The 10 ml collected fractions shown to be pure bis-N-oxide by thin layer chromatography (TLC eluting system:methylene chloride:methanol:concentrated ammonium hydroxide=6:1:0.1; vanillin:85% H₃PO₄:ethanol spray indicator used with heat on silica gel plates) were combined. From 1 gram of crude product, 128 mg of pure bis-oxide was obtained. ¹Hnmr (CDCl₃) delta 3.20

[9H, broad s, aglycone CH₃—N⁺—→O⁻ and (CH₃)₂—N⁺—→O⁻], 3.39 (3H, s, cladinose CH₃O-); MS: m/e 461, and 431, 415 (these two peaks are diagnostic for aglycone N-oxide), 159 (cladinose derived fragment), 115 (desosamine N-oxide derived fragment).

The above-described chromatographic procedure also afforded a second, less polar product from the crude: N-methyl-11-aza-10-deoxo-10-dihydroerythromycin A desosaminyl-N-oxide (246 mg).

¹Hnmr (CDCl₃) delta 2.30

(3H, s, aglycone CH₃—N—), 3.18 [6H, s, (CH₃)₂—N⁺—→O⁻], 3.37 (3H, s, cladinose CH₃O-); MS: major peaks at m/e 461, 156, 115.

EXAMPLE 3

N-Methyl-11-aza-10-deoxo-10-dihydroerythromycin A

A solution of the crude product of Example 2, comprising N-methyl-11-aza-10-deoxo-10-dihydroerythromycin A desosaminyl-N-oxide and N-methyl-11-aza-10-deoxo-10-dihydroerythromycin A bis-N-oxide (4.36 g), in 150 ml of absolute ethanol was hydrogenated on a Parr apparatus (3.52 kg/m²; 8.0 g 10% palladium on carbon catalyst; ambient temperature) for 1¼ hours. The catalyst was filtered, and the resulting filtrate was evaporated to dryness, affording a colorless foam (4.3 g). The crude product was taken up in methylene chloride (100 ml) and then stirred with water (100 ml) while the pH of the mixture was adjusted to 8.8. The organic and aqueous layers were separated. The aqueous layer was then extracted twice with 50 ml portions of methylene chloride. The three organic extracts were combined, dried over anhydrous sodium sulfate and evaporated to afford a colorless foam (3.0 g). The entire sample was dissolved in 11 ml of warm ethanol, and water was added until the solution became slightly turbid. Upon standing overnight, 1.6 g of the title product crystallized from solution; m.p.136° C., dec. A recrystallization by the same procedure raised the melting point to 142° C., dec. ¹Hnmr (CDCl₃) delta 2.31 [6H, s, (CH₃)₂N-], 2.34

(3H, s, aglycone CH₃—N—);

¹³Cnmr [CDCl₃, (CH₃)₄Si internal standard] ppm 178.3 (lactone, C=O), 102.9 and 94.8 (C-3, C-5), 41.6

(aglycone CH₃—N—), 40.3 [(CH₃)₂-N-]; MS: m/e 590, 432, 158.

EXAMPLE 4

N-Methyl-11-aza-10-deoxo-10-dihydroerythromycin A

The pure N-methyl-11-aza-10-deoxo-10-dihydroerythromycin A bis-N-oxide of Example 2 (20 mg) was hydrogenated according to the procedure of Example 3. Thin layer chromatography with the system methylene chloride:methanol:concentrated ammonium hydroxide (9:1:0.1) and the use of a vanillin spray as indicator (see Example 2) with heat on silica gel plates showed a single, uniform product. Its ¹Hnmr and TLC Rf values were identical to those of the product of Example 3. Yield: 60%.

EXAMPLE 5

N-Methyl-11-aza-10-deoxo-10-dihydroerythromycin A

A solution of crude product of Example 2 comprising N-methyl-11-aza-10-deoxo-10-dihydroerythromycin A desosaminyl-N-oxide and N-methyl-11-aza-10-deoxo-10-dihydroerythromycin A bis-N-oxide (10.0 g) in 150 ml of absolute ethanol was hydrogenated on a Parr apparatus [3.52 kg/m²; 15 g of Raney-Nickel catalyst (water-wet sludge); ambient temperature] for 1½ hours. Work-up as described in Example 3 afforded 8.5 g of the title product, with TLC Rf values identical to those of Example 3.

EXAMPLE 6

N-Methyl-11-aza-10-deoxo-10-dihydroerythromycin A

A solution of N-methyl-11-aza-10-deoxo-10-dihydroerythromycin A desosaminyl-N-oxide (15 mg) in ethanol (5 ml) was hydrogenated at 2 psi using 5 mg 5% Pd-C catalyst for 3 hours. Filtration of the catalyst and solvent removal in vacuo produced the title compound (98% yield) as a colorless foam. Its ¹Hnmr and TLC Rf values were identical to those of the product of Example 3.

EXAMPLE 7

N-Methyl-11-aza-10-deoxo-10-dihydroerythromycin A Hydrochloride

To a solution of N-methyl-11-aza-10-deoxo-10-dihydroerythromycin A (0.2 g, 0.27 mmole) in 50 ml of ethanol (absolute) is added an equimolar amount of hydrogen chloride and the reaction mixture stirred at room temperature for one hour. Removal of the solvent by evaporation under reduced pressure affords the mono-hydrochloride salt.

In like manner, the hydrobromide, acetate, sulfate, butyrate, citrate, glycolate, stearate, pamoate, p-toluenesulfonate, benzoate and aspartate salts of N-methyl-11-aza-10-deoxo-10-dihydroerythromycin A, are prepared.

Repetition of this procedure but using twice the amount of acid affords the di-acid salts of said N-methyl derivative.

EXAMPLE 8

N-Methyl-11-aza-10-deoxo-10-dihydroerythromycin A bis-Hydrochloride

To a solution of 2.00 g of N-methyl-11-aza-10-deoxo-10-dihydroerythromycin A in 50 ml of methylene chloride, a solution of 308 mg of pyridinium hydrochloride in 25 ml of methylene chloride was added dropwise over several minutes. The mixture was concentrated to a brittle foam (2.35 g), was thoroughly pulverized in the presence of 125 ml of water. The clear aqueous solution was decanted from the water-insoluble residue and lyophilized to afford the bis-hydrochloride salt of N-methyl-11-aza-10-deoxo-10-dihydroerythromycin A as a colorless amorphous foam (1.21 g).

Analysis: Calc'd. for $C_{38}H_{72}O_{12}N_2 \cdot 2HCl$: 8.65% Cl; Found: 8.89% Cl.

Treatment of a small portion of the water-soluble product with aqueous sodium bicarbonate afforded a water-insoluble product having identical TLC Rf characteristics to those described above for N-methyl-11-aza-10-deoxo-10-dihydroerythromycin A free base.

EXAMPLE 9

2',4"-Diacetyl-N-methyl-11-aza-10-deoxo-10-dihydroerythromycin A

A solution of N-methyl-11-aza-10-deoxo-10-dihydroerythromycin A (1.5 g, 2 mmole) in pyridine (50 ml) and acetic anhydride (30 ml) is allowed to stand at room temperature for 3 days. It is then poured over ice and the pH adjusted to 9 with 20% NaOH (w/w) solution. Extraction of the mixture with chloroform (3×50 ml) followed by drying the combined extracts (over $K_2CO_3$) and evaporation of the solvent under reduced pressure affords the title compound.

Repetition of this procedure but using propionic anhydride or 3-carbethoxypropionic anhydride as acylating agents affords the appropriate 2',4"-diacyl derivatives.

EXAMPLE 10

4"-Acetyl-N-methyl-11-aza-10-deoxo-10-dihydroerythromycin A

2',4"-Diacetyl-N-methyl-10-deoxo-10-dihydroerythromycin A (1.0 g) is dissolved in 100 ml of methanol and allowed to stand 3 days at room temperature. Evaporation of the methanol under reduced pressure affords the title product.

Solvolysis of the 2',4"-dipropionyl- and the 2',4"-3-carbethoxypropionyl derivatives of Example 9 affords the corresponding 4"-propionyl- and 4"-(3-carbethoxypropionyl)-derivatives.

I claim:

1. A compound of the formula

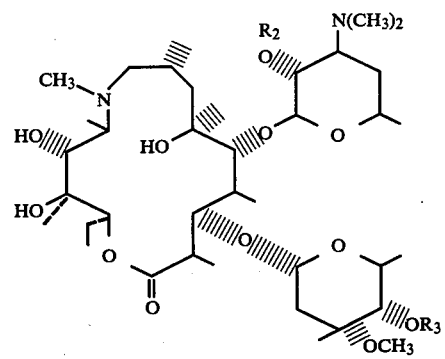

or a pharmaceutically acceptable acid addition salt thereof wherein
$R_2$ is hydrogen, alkanoyl having from 2 to 3 carbon atoms or 3-carbethoxypropionyl;
$R_3$ is hydrogen, alkanoyl having from 2 to 3 carbon atoms or 3-carbethoxypropionyl.

2. A compound according to claim 1 wherein each of $R_2$ and $R_3$ is hydrogen.

3. A compound having the formula

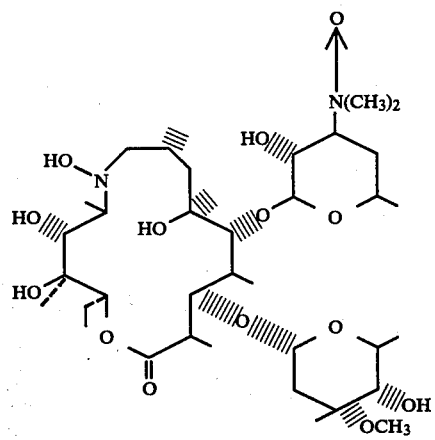

4. A compound having the formula

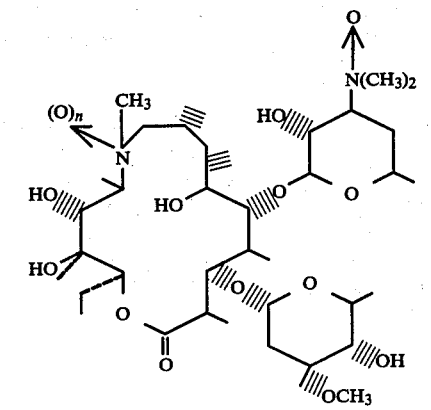

wherein n is 0 or 1.

5. The compound of claim 4 wherein n is 1.
6. The compound of claim 4 wherein n is 0.
7. A method for treating a bacterial infection in a mammal which comprises administering to a mammal having said infection an antibacterially effective amount of a compound of claim 1.
8. A pharmaceutical composition having antibacterial activity which comprises an antibacterially effective amount of a compound of claim 1 and a pharmaceutically acceptable carrier.

* * * * *